(12) United States Patent
Shin et al.

(10) Patent No.: US 9,239,325 B2
(45) Date of Patent: Jan. 19, 2016

(54) MICROCHIP-BASED APPARATUS FOR EXAMINING PLATELET COMPOSITE FUNCTIONS

(75) Inventors: Se Hyun Shin, Seoul (KR); Jeong Hun Nam, Seoul (KR); Chae Seung Lim, Anyang-si (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 14/237,667

(22) PCT Filed: Aug. 9, 2012

(86) PCT No.: PCT/KR2012/006338
§ 371 (c)(1),
(2), (4) Date: Feb. 7, 2014

(87) PCT Pub. No.: WO2013/022284
PCT Pub. Date: Feb. 14, 2013

(65) Prior Publication Data
US 2015/0010995 A1    Jan. 8, 2015

(30) Foreign Application Priority Data

Aug. 10, 2011    (KR) ........................ 10-2011-0079497

(51) Int. Cl.
*G01N 33/50*    (2006.01)
*G01N 33/49*    (2006.01)
(Continued)

(52) U.S. Cl.
CPC ........ *G01N 33/5044* (2013.01); *B01F 13/0818* (2013.01); *B01L 3/5027* (2013.01);
(Continued)

(58) Field of Classification Search
CPC ........... B01L 3/5027; B01L 2300/0861; B01F 13/0818; B01F 13/0059; B01F 5/0653; G01N 33/4905
See application file for complete search history.

(56) References Cited

U.S. PATENT DOCUMENTS 5,024,237 A *  6/1991  Guirguis ....................... 600/573
5,302,348 A    4/1994  Cusack et al.
(Continued)

FOREIGN PATENT DOCUMENTS

CN      1806171 A         7/2006
JP      2003344391 A *   12/2003    ............. G01N 33/49
(Continued)

OTHER PUBLICATIONS

Extended European Search Report for Application No. EP 12821927.6, issued Jun. 19, 2015. (7 Pages).

*Primary Examiner* — Jill Warden
*Assistant Examiner* — Matthew Krcha
(74) *Attorney, Agent, or Firm* — Mintz Levin Cohn Ferris Glovsky and Popeo, P.C.; Fred C. Hernandez; Linyu L. Mitra

(57) ABSTRACT

There is provided a microchip-based platelet multi-function test apparatus. The apparatus includes a sample container configured to accommodate a blood sample therein, a stirrer that is installed inside the sample container and induces a shear flow in the blood sample, a parallel channel configured to divide and flow the blood stirred by the stirrer into a plurality of paths, a vacuum device that is connected to an end of each parallel channel, maintains constant pressure, allows the stirred blood to flow along the parallel channel, a light source that is installed in a rear side of the parallel channel and radiates light to the parallel channel, and an image sensor that receives light transmitted through the blood in the parallel channel, converts the light into an electrical signal, and measures a flowing distance of a blood flow.

6 Claims, 2 Drawing Sheets

(51) Int. Cl.
 *B01L 3/00* (2006.01)
 *B01F 13/08* (2006.01)
(52) U.S. Cl.
 CPC ......... *G01N33/4905* (2013.01); *B01L 2200/16* (2013.01); *B01L 2300/0816* (2013.01); *B01L 2300/0864* (2013.01); *B01L 2400/049* (2013.01); *B01L 2400/0475* (2013.01)

(56) References Cited

U.S. PATENT DOCUMENTS

| | | | |
|---|---|---|---|
| 2002/0013343 A1* | 1/2002 | Serebruany et al. | 514/321 |
| 2003/0017467 A1* | 1/2003 | Hooper et al. | 435/6 |
| 2003/0138941 A1* | 7/2003 | Gong et al. | 435/287.2 |
| 2008/0038839 A1* | 2/2008 | Linder et al. | 436/501 |
| 2010/0267066 A1* | 10/2010 | Hosokawa et al. | 435/13 |
| 2011/0151500 A1* | 6/2011 | Hosokawa et al. | 435/29 |

FOREIGN PATENT DOCUMENTS

| | | |
|---|---|---|
| JP | 2008-539438 A | 11/2008 |
| JP | 2010-539503 A | 12/2010 |
| KR | 20030032809 A | 4/2003 |
| KR | 20100098107 A | 9/2010 |
| KR | 20100098656 A | 9/2010 |
| KR | 20110056497 A | 5/2011 |
| WO | WO-2006/066008 A2 | 6/2006 |
| WO | WO-2006/116361 A2 | 11/2006 |
| WO | WO-2008/072870 A1 | 6/2008 |
| WO | 2009069656 A1 | 6/2009 |
| WO | 2010009267 A1 | 1/2010 |
| WO | 2010018833 A1 | 2/2010 |
| WO | WO-2011066361 A1 | 6/2011 |

* cited by examiner

MICROCHIP-BASED APPARATUS FOR EXAMINING PLATELET COMPOSITE FUNCTIONS

CROSS-REFERENCE TO RELATED APPLICATIONS

This application is a national stage application, filed under 35 U.S.C. §371, of International Application No. PCT/KR2012/006338, filed Aug. 9, 2012, which claims priority under 35 USC 5 §119(a) of a Korean Patent Application No. 10-2011-0079497 filed on Aug. 10, 2011, the contents of which are incorporated herein by reference in their entireties.

BACKGROUND OF THE INVENTION

1. Field of the Invention

The present invention relates to a platelet multi-function test apparatus, and more specifically, to a microchip-based platelet multi-function test apparatus that can automatically test a small amount or a large amount of sample through a flow path design of a microchip.

2. Description of the Related Art

A platelet function test is widely used for screening congenital platelet dysfunctions or a preoperative screening test, and particularly, is an important test for screening a hemorrhagic disease due to congenital or acquired platelet dysfunction in hemorrhagic diseases having no numerical platelet disorders.

Recently, this platelet function test is being widely used to test increased bleeding tendency due to an antiplatelet drug used for treatment and prevention of a cardiovascular disease and to test drug resistance.

A bleeding time (BT) test is a bleeding time measurement test that is developed about 100 years ago and is used as a platelet function screening test up to present. However, a currently used platelet function test has problems in that it is difficult to standardize, clinical usefulness is low, and an invasive method is required. Therefore, an objective measurement method capable of measuring a platelet function is required.

In a platelet function analyzer (for example, PFA-100) used as technology that is designed to address the aforementioned problems and used to measure a function of platelets, there is a characteristic in that platelets are aggregated due to von Willebrand factor (vWF) activated at a high shear rate. In order to measure this characteristic, a method has been performed such that whole blood flows into a long capillary tube at a high shear rate, and then a closure time, which is a time for clogging an orifice pore by aggregation of platelets to an orifice coated with collagen and either ADP or epinephrine, is measured using pressure or flux.

In order to perform this platelet function test, there is a problem in that it is absolutely dependent on a function of vWF, a test dependent on hematocrit (Hct) is performed, and an anti-aspirin or anti-clopidogrel test cannot be performed. In addition, in order to perform a platelet function test, two phases of tests are necessary, which results in an increased test cost.

In particular, in order to activate vWF, a blood sample is required to be exposed for a predetermined time or more at a high shear rate. To this end, PFA-100 uses a method in which blood flows within a relatively long capillary tube at a high speed. However, this method has a problem in that a large amount of blood is required, vWF near a capillary tube wall having a maximum shear rate is easily activated, but vWF positioning in a tube center having a minimum shear rate is not activated. For this reason, there may be a problem of repeatability of a test result.

SUMMARY OF THE INVENTION

In view of the aforementioned problems, the present invention provides a microchip-based platelet multi-function test apparatus capable of performing a multi-test of a composite platelet function through a single test, reducing a test cost, and increasing test repeatability and accuracy.

The present invention also provides a microchip-based platelet multi-function test apparatus that has a structure capable of automatically measuring a closure time.

Technical challenges of the invention are not limited to the above technical challenges and another technical challenge not mentioned above may be apparently understood by those skilled in the art from the following description.

According to an aspect of the invention, there is provided a microchip-based platelet multi-function test apparatus. The apparatus may include a sample container configured to accommodate a blood sample therein, a stirrer that is installed inside the sample container and induces a shear flow in the blood sample, a parallel channel configured to divide and flow the blood stirred by the stirrer into a plurality of paths, a vacuum device that is connected to an end of each parallel channel, maintains constant pressure, allows the stirred blood to flow along the parallel channel, a light source that is installed in a rear side of the parallel channel and radiates light to the parallel channel, and an image sensor that receives light transmitted through the blood in the parallel channel, converts the light into an electrical signal, and measures a flowing distance of a blood flow.

According to another aspect of the invention, there is provided a microchip-based platelet multi-function test apparatus. The apparatus may include a sample container configured to accommodate a blood sample therein, a stirrer that is installed inside the sample container and induces a shear flow in the blood sample, a parallel channel configured to divide and flow the blood stirred by the stirrer into a plurality of paths, a vacuum device that is connected to an end of each parallel channel, and allows the stirred blood to flow along the parallel channel, a vacuum valve configured to control opening and closing of the vacuum device and a plurality of parallel channels, and a pressure sensor that measures decrease of initial vacuum pressure over time in the parallel channel, and calculates a time in which the measured vacuum pressure is not decreased over time.

A sudden extension part of a flow path for reducing a blood flow rate may be installed in a front end of the parallel channel.

A plurality of micropillars that reduce a blood flow rate and allow platelets to be adhered and aggregated for a platelet function test may be installed in a front end of the parallel channel.

The micropillar may be coated with either a reagent of collagen and epinephrine or a reagent of collagen and ADP.

The micropillar positioned in each parallel channel may be coated with a different reagent.

A chamber having a plurality of beads therein may be installed in a front end of the parallel channel.

A through hole having a diameter smaller than that of the bead may be formed in a front surface and a rear surface of the chamber.

The bead may be coated with either a reagent of collagen and epinephrine or a reagent of collagen and ADP.

The bead positioned in each parallel channel may be coated with a different reagent.

The vacuum device may include a vacuum chamber that is connected to an end of the parallel channel, and a syringe that is connected to the vacuum chamber and in which a piston is movably installed therein and maintains the vacuum chamber with constant pressure.

A vacuum valve for controlling opening and closing of the parallel channel may be further installed between the vacuum chamber and the syringe.

A minimum shear rate may be 5000 ($s^{-1}$) or more or minimum shear force may be 8 Pa or more, which is caused by stirring of the stirrer.

The light source may be an LED array and the image sensor may be a CCD sensor.

After the blood sample is injected, the vacuum valve may be opened such that vacuum pressure of the vacuum chamber is connected to the parallel channel, may be immediately closed, and thereby initial vacuum pressure of each parallel channel may be decreased according to flowing of the blood sample.

According to the invention, blood stirred at a high shear rate is injected to a parallel channel, and a test may be performed with a different reagent in each channel. Therefore, it is possible to perform a multi-test on a composite platelet function through a single test and reduce a test time and a test cost.

According to the invention, a flowing distance of a blood flow is measured using an image sensor and a light source installed in a rear end of the parallel channel, constant pressure is maintained using a syringe, and thus it is possible to easily determine a closure time.

In addition, vWF existing inside a blood sample is homogeneously activated by applying shear force for a predetermined time or more in a relatively uniform shear flow field. Therefore, it is possible to improve repeatability of a platelet aggregation phenomenon.

DETAILED DESCRIPTION

Hereinafter, a microchip-based platelet multi-function test apparatus according to an embodiment of the invention will be described in detail with reference to the accompanying drawings.

Figure 1:
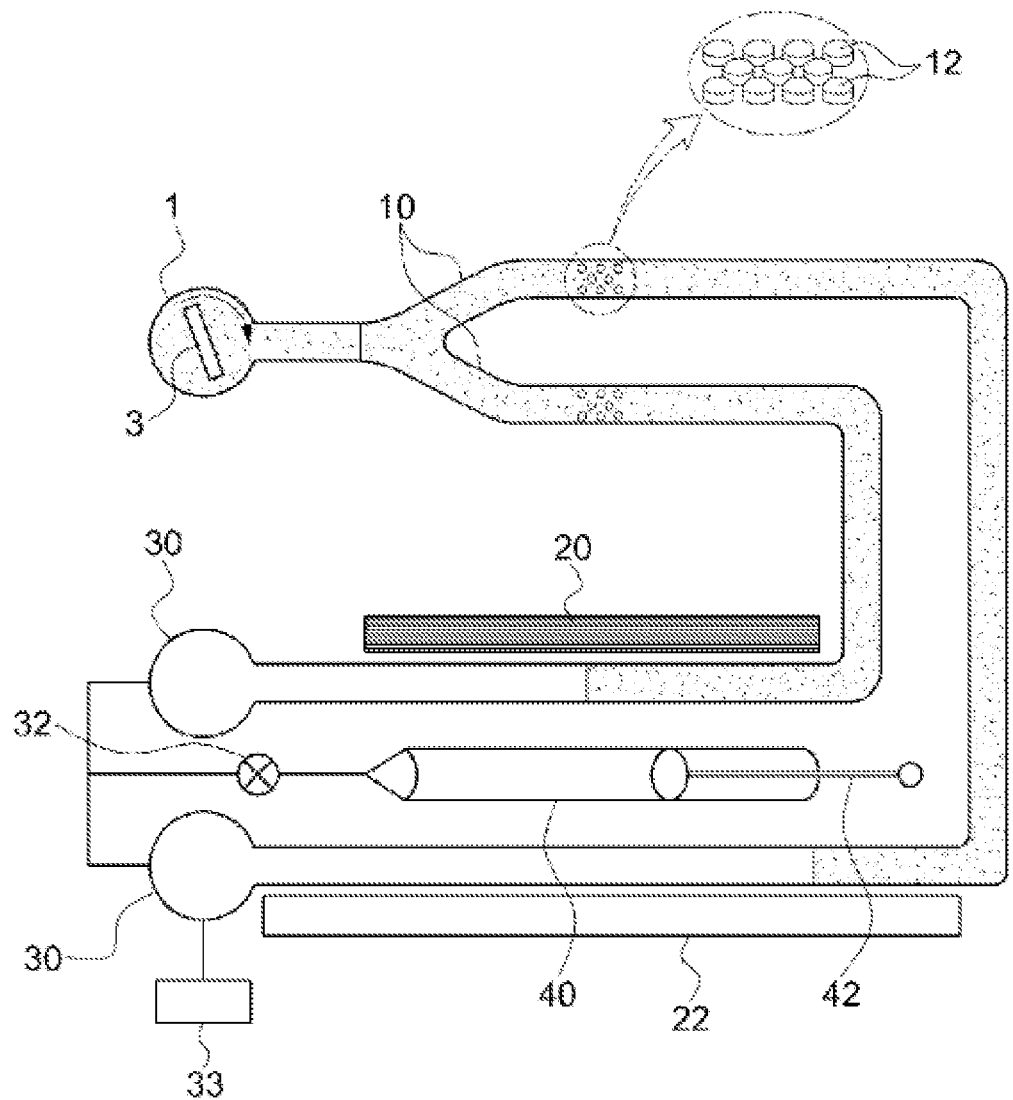
FIG. 1 is a diagram illustrating a configuration of a microchip-based platelet multi-function test apparatus according to an embodiment of the invention.
Figure 2:
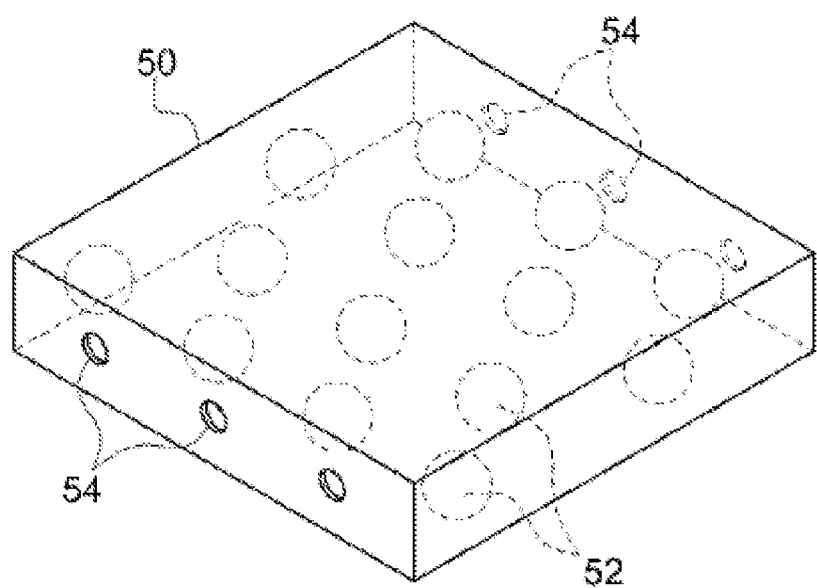
FIG. 2 is a diagram illustrating a configuration of a chamber having a plurality of beads of the microchip-based platelet multi-function test apparatus according to the invention.

FIG. 1 is a diagram illustrating a configuration of a microchip-based platelet multi-function test apparatus according to an embodiment of the invention.

As illustrated, the microchip-based platelet multi-function test apparatus according to the invention includes a sample container 1 in which a blood sample is accommodated. The sample container 1 is made in a form of a substantially circular chamber. A size of the sample container 1 may be manufactured in various sizes depending on purposes. In addition, it is preferable that the sample container 1 be optically transparently manufactured so as to be easily observed from the outside.

Next, a stirrer 3 is installed inside the sample container 1. A shape of the stirrer 3 may be configured as either a round bar or a round plate. Alternatively, the stirrer 3 may be configured as a shape other than the above shape. It is preferable that a diameter or a thickness of the stirrer 3 be about a half size of a depth of the sample container 1. It is appropriate that a length or a diameter of the stirrer 3 is a size of about 80% to 90% of a diameter of the sample container 1. In this case, it is preferable that a minimum shear rate be 5000 ($s^{-1}$) or more or minimum shear force be 8 Pa or more, which is caused by rotation of the stirrer 3. In addition, it is preferable that an exposure time of the blood sample to a shear flow field be at least 30 seconds or more. This is performed in order to sufficiently activate vWF using the shear rate.

The stirrer 3 performs rotation movement at an appropriate rate so that a high shear flow is induced in the blood sample injected to the sample container 1, vWF in the blood is activated, and platelets can be adhered and aggregated to a portion coated with an appropriate reagent. The stirrer 3 may be made of a thin metal material such that it is magnetized by magnetic force of a device for inducing stirring (not illustrated) that is separately installed and is affected without a mechanical connection. In addition, the stirrer 3 may have a bar or a pipe shape as illustrated in FIG. 1 or may be made to have a round plate, a cone shape having a slight slope and thickness, or a bead shape.

Meanwhile, the blood sample supplied from the sample container 1 is divided and flows into a parallel channel 10 having a plurality of paths. Although the parallel channel 10 is illustrated as two channels in FIG. 1, the invention is not limited thereto but the parallel channel may be divided and configured into three or more channels. A parallel channel configuration in this embodiment is to perform a multi-function test of the blood sample at once by coating different types of reagents for each channel. In addition, it is possible to perform a detailed, precise test on a plurality of platelet functions through a single test, and decrease a test cost and a test time.

A micropillar 12 may be coated with either a reagent of collagen and epinephrine or a reagent of collagen and ADP. For example, in the parallel channels 10 illustrated in FIG. 1, an upper channel may be coated with a mixture of collagen and epinephrine and a lower channel may be coated with a mixture of collagen and ADP. This reagent may be coated on a channel wall or a surface of a bead 54 or the micropillar 12 to be described.

A plurality of protruding micropillars 12 are installed in the parallel channel 10, and it is preferable that the micropillar 12 be installed in a front end of the parallel channel 10. The micropillar 12 is coated with the above reagent, increases a contact area of platelets with a coating portion, and decreases a blood flow. That is, a structure section in which a flow cross-section area is obstructed is configured such that platelets are smoothly adhered to a contact area with an enlarged reagent coating portion according to a section in which vWF activated by a high shear flow reacts with platelets and thus a flow decreases.

Meanwhile, there is no need to perform the above function using only the micropillar 12. As illustrated in 2, in the parallel channel 10, a separate chamber 50 may be installed in a position in which the micropillar 12 is installed. The chamber 50 is made to have a substantially rectangular parallelepiped shape and a space is formed therein which allows blood to pass.

In addition, a through hole 52 is formed in a front surface and a rear surface of the chamber 50 and thus blood is supplied and discharged. A plurality of beads 54 having a diameter greater than that of the through hole 52 are provided inside the chamber 50. The bead 54 is coated with a reagent such as a mixture of collagen and epinephrine, increases a contact area of platelets with a coating portion, and decreases a blood flow like in the micropillar 12.

Meanwhile, although not specifically illustrated, a sudden extension part of a flow path for reducing a blood flow rate may be installed in a front end of the parallel channel 10, that is, a front of a part in which the micropillar 12 or the chamber 50 is installed.

A light source 20 for radiating light to the parallel channel 10 is installed in a rear side of the parallel channel 10. An image sensor 22 is installed in an opposite side of the light source 20 interposing the parallel channels 10 therebetween. The image sensor 22 receives light radiated from the light source 20, converts the light into an electrical signal, and measures a flowing distance of the blood flow in real time. That is, light radiated from the light source 20 is received in the image sensor 22 through the blood flowing into the parallel channel 10, an amount of light received in the image sensor 22 is reduced when the blood is filled therein, and thus this reduction is used to measure the flowing distance of the blood flow.

In this manner, when the flowing distance of the blood flow is measured, it is possible to measure a closure time of platelets. For example, when a flux falling below 10% of an initial flux continues for three seconds or more, this time can be considered as the closure time.

Meanwhile, an LED array or the like may be used as the light source 20 and a CCD sensor may be used as the image sensor 22.

Next, a vacuum device for maintaining constant pressure inside of the parallel channel 10 is installed in an end of the parallel channel 10. The vacuum device includes a vacuum chamber 30 connected to the end of the parallel channel 10 and a syringe 40 for maintaining constant pressure in the vacuum chamber 30. Here, a vacuum valve 32 is provided between the vacuum chamber 30 and the syringe 40, and a piston 42 is movably installed in the syringe 40 and performs a vacuum suction operation. The vacuum valve 32 controls opening and closing of the vacuum device and the plurality of parallel channels 10.

That is, the piston 42 maintains rated vacuum by moving backward inside the syringe 40 at a position in which the blood flow begins. When the vacuum valve opens, reducing pressure is measured, the syringe 40 is retracted by a degree corresponding to the reduced pressure, and thus pressure of the syringe and a connected pipe is constantly maintained. In this case, unlike PFA-100, in terms of a sample flow rate according to the invention, there is no need to quickly flow. Thus, the sample flows in an appropriate rate, and rated pressure necessary for flowing may be provided.

That is, whereas PFA-100 uses a method of activating vWF through a rapid capillary tube shear flow, a rapid flow is unnecessary in the present invention since vWF is already activated through a shear flow generation mechanism of the sample container.

Meanwhile, a pressure sensor 33 for measuring press, that is reduced over time in the vacuum device, is connected to a side of the vacuum chamber 30.

In addition, in the vacuum device, the parallel channel 10 is connected to the vacuum chamber 30 having constant vacuum pressure. When the piston 42 is fixed, the blood sample flows into the parallel channel 10 due to the vacuum pressure and the pressure is gradually reduced, accordingly. That is, after the blood sample is injected, the vacuum valve 32 is opened such that vacuum pressure of the vacuum chamber 30 is connected to the parallel channel 10, and is immediately closed. Therefore, initial vacuum pressure of each parallel channel 10 is decreased according to flowing of the blood sample. In this way, when pressure decreases over time in the vacuum device and a time point having no longer pressure change arrives, this time point may be replaced as the closure time.

Hereinafter, a platelet multi-function test method having the configuration as described above according to the invention will be described in detail.

First, an inspector injects a blood sample collected by venipuncture to the sample container 1. Then, the stirrer 3 installed in the sample container 1 is driven. Here, stirring of the blood sample may be performed through rotating at a predetermined rate and for a predetermined time. According to this stirring, vWF is activated.

Next, the blood sample flows into different paths through the parallel channels 10. Here, the activated vWF adheres to the reagent (a mixture of collagen and epinephrine or a mixture of collagen and ADP) that are coated on the micropillar 12 or the bead 54, which makes a foundation for adhering platelets. In this way, using different reagents coated on each parallel channel 10, it is possible to perform a detailed, precise test on a plurality of platelet functions.

Meanwhile, a flowing distance of the blood flow in the parallel channel 10 is measured using the light source 20 and the image sensor 22. That is, light radiated from the light source 20 passes through the blood in the parallel channel 10, is received in the image sensor 22, is converted into an electrical signal in the image sensor 22, and thus a flowing distance of the blood is measured in real time. In the measuring process as described above, when a flux falling below 10% of an initial flux continues for three seconds or more, this time can be defined as the closure time. In this case, the piston 42 of the syringe 40 is retracted according to the blood flow, controls it with constant pressure, calculates a flux, and thus determines the closure time.

The scope of the invention is not limited to the one or more embodiments described above but defined by claims to described below. It is obvious that those of ordinary skill in the art can variously modify and adapt within the scope of the claims.

What is claimed is:

1. A microchip-based platelet multi-function test apparatus, comprising:
    a sample container configured to accommodate a blood sample therein;
    a stirrer that is installed inside the sample container and induces a shear flow in the blood sample;
    at least a first and a second parallel channel configured to divide and flow the blood stirred by the stirrer into a plurality of paths;
    a vacuum device that is connected to an end of each parallel channel, maintains constant pressure, allows the stirred blood to flow along the parallel channel;
    a light source that is installed in a rear side of the parallel channel and radiates light to the parallel channel; and
    an image sensor that receives light transmitted through the blood in the parallel channel, converts the light into an electrical signal, and measures a flowing distance of a blood flow,
    wherein a plurality of micropillars that reduce a blood flow rate and allow platelets to be adhered and aggregated for a platelet function test are installed in a front end of the parallel channel,
    wherein the micropillars positioned in each parallel channel are coated with either a reagent of collagen and epinephrine or a reagent of collagen and ADP.

2. A microchip-based platelet multi-function test apparatus, comprising:

a sample container configured to accommodate a blood sample therein;

a stirrer that is installed inside the sample container and induces a shear flow in the blood sample;

at least a first and a second parallel channel configured to divide and flow the blood stirred by the stirrer into a plurality of paths;

a vacuum device that is connected to an end of each parallel channel, and allows the stirred blood to flow along the parallel channel;

a vacuum valve configured to control opening and closing of the vacuum device and a plurality of parallel channels; and a pressure sensor that measures decrease of initial vacuum pressure over time in the parallel channel, and calculates a time in which the measured vacuum pressure is not decreased over time, wherein a plurality of micropillars that reduce a blood flow rate and allow platelets to be adhered and aggregated for a platelet function test are installed in a front end of the parallel channel, wherein the micropillars positioned in each parallel channel are coated with either a reagent of collagen and epinephrine or a reagent of collagen and ADP.

3. The apparatus according to claims 1 or 2, wherein the micropillars positioned in the first parallel channel are coated with collagen and epinephrine and the micropillars positioned in the second parallel channel are coated with collagen and ADP.

4. The apparatus according to claim 1, wherein the vacuum device includes:

a vacuum chamber that is connected to an end of the parallel channel; and a syringe that is connected to the vacuum chamber and in which a piston is movably installed therein and maintains the vacuum chamber with constant pressure.

5. The apparatus according to claim 4, wherein a vacuum valve for controlling opening and closing of the parallel channel is further installed between the vacuum chamber and the syringe.

6. The apparatus according to claim 2, wherein, after the blood sample is injected, the vacuum valve is opened such that vacuum pressure of the vacuum chamber is connected to the parallel channel, is immediately closed, and thereby initial vacuum pressure of each parallel channel is decreased according to flowing of the blood sample.

\* \* \* \* \*